Oct. 7, 1941. J. W. STEIDLE, JR Plant Pat. 491
CARNATION
Filed May 15, 1941
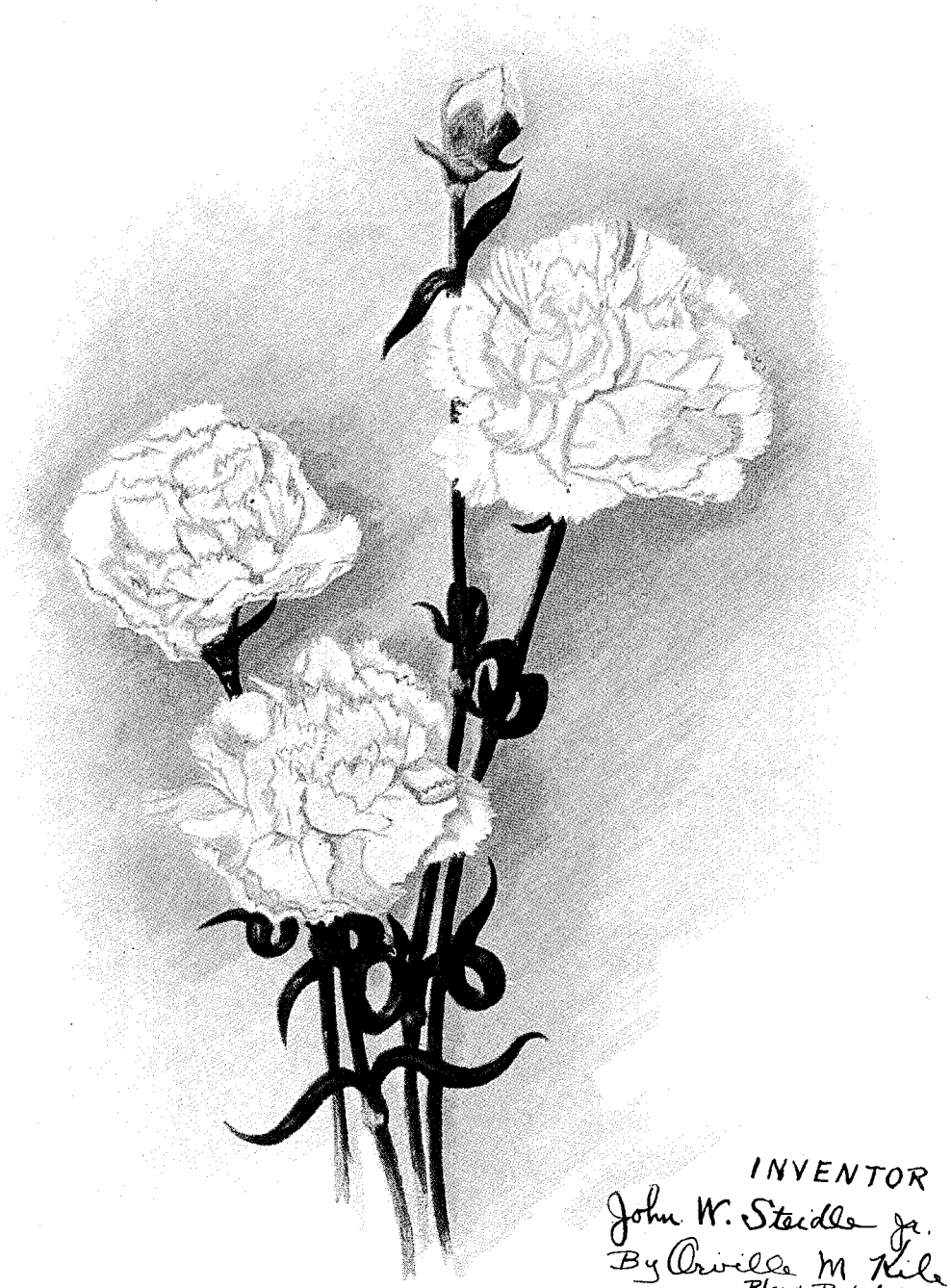
INVENTOR
John W. Steidle Jr.
By Orville M. Kile
Plant Pat Agt.

Patented Oct. 7, 1941

Plant Pat. 491

UNITED STATES PATENT OFFICE

491

CARNATION

John W. Steidle, Jr., St. Louis County, Mo.

Application May 15, 1941, Serial No. 393,621

1 Claim. (Cl. 47—60)

My new invention relates to improvements in the class generally known as greenhouse forcing carnations, and is the result of definite breeding efforts carried on by me at my greenhouses in St. Louis County. This new variety resulted as a cross between the varieties Senator and Golden Wonder. The purpose of this breeding effort was to produce a healthy, strong-growing carnation plant with pure white blossoms of good size and substance.

The new variety is more nearly like its parent, Senator, than any other variety known to me yet it differs materially from that variety, many of the differences being a matter of degree. The new variety is a much stronger grower in all stages; has a more evenly formed flower, the size of which is more consistent in all weathers and the petals of which are of much thicker substance; and has a more slowly opening bud and flower, with a consequently longer keeping period when used as a cut flower.

My new variety is also somewhat similar to Patrician although its growth is much higher and not so heavy as that of Patrician and it has a pure white flower whereas the flower of Patrician has a pink flake. The new flower has petals of much greater substance, although the petalage is not so great, and the flowers have a more perfect form than those of Patrician.

Asexual reproduction of my new variety for several years has shown its qualities to be permanently fixed.

The original illustration accompanying this application shows a bud and three flowers of the new variety, together with stems and foliage. The shadings of gray and cream on the flowers in the paintings are the artist's portrayal of lights and shadows and should not be considered a color of the flower, which is pure white throughout.

Following is a detailed description of the flower and plant characteristics. Color plate references indicate Ridgway's Color Standards and Nomenclature.

*The plant*

Growth habit: Strong and vigorous, attains a height of about three feet. Produces many side shoots; propagates and roots easily.

Blooming habit: Continuous bloomer; prolific in production of large flowers, the size remaining large even in warm weather.

Stems: Strong; erect; very long, approximately 3 feet; color between Empire Green (Plate XXXII) and Dusky Yellowish Green (Plate XLI); slightly glaucous. Internodes are very long on upper portion of stem, diminishing in length toward the base.

Foliage: Approximately Dark Dull Yellow Green (Plate XXXII). New foliage of sideshoots is Forest Green (Plate XVII) at their tips, blending into Light Yellow Green (Plate VI) where they join the main stem. Leaves are long and curled. Upper leaves are of average width but lower ones are exceptionally wide for carnation foliage—about ½ inch. Although the quantity is normal, it appears abundant because of the great size. Substance is heavy and waxy.

*The flower*

Bud: Unopened bud is short and blunt. As it opens, the calyx lengthens to become about one-half the total bud length which is 1¾ to 2 inches just before unfurling. Bud opens very slowly and in such a manner as to somewhat resemble a pinwheel until it attains the "perfect" formation when fully opened.

Blossom:

*Shape.*—When fully opened the blossom is regular and high-centered. Outer petals lie in a plane at right angles to stem, forming almost a perfect circle. Although the petalage is not great the arrangement of the petals and their very heavy substance gives the appearance of a very large, full flower.

*Size.*—Large, under usual greenhouse conditions averaging 3½ inches in diameter.

*Petalage.*—From 40 to 45 petals in early April, including all small central petals.

*Color.*—Pure white throughout.

*Petals.*—Petals of the two or three outer rows are very broad, uncrinkled, and regular in shape, with very shallow marginal notches. Length, including shank, is 2⅜ to 2½ inches. Width is slightly more thatn 1½ inches. Other petals are progressively smaller toward the center and are less regularly placed. Texture of the petals is much more substantial than that of any other white carnation known to me.

*Calyx.*—Tough, preventing splitting; campanulate or bell-shaped, opening sufficiently wide to let the petals spread into a large-appearing flower without being ragged. Three-fourths to one inch broad at top. Very much lighter in color than the stems and foliage—approximately Parrot Green (Plate VI).

*Bracts.*—Six; broad; acutely pointed; points darker in color than calyx.

*Fragrance.*—Intense cinnamon fragrance; very pleasing.

*Keeping qualities.*—Flower lasts well on plant. As a cut flower it keeps better than any other known white variety and better than most varieties of other colors.

Reproductive organs:

*Pistils.*—Two; white; tapering and gently curved; 1½ to 1¾ inches in length.

*Stamens.*—Few; short; greenish white.

*Ovary.*—Relatively small; ovules few or lacking.

Having thus disclosed my invention, I claim:

The new and distinct variety of carnation with qualities in combination herein shown and described, characterized particularly by its heavy growth; its unusually wide, dark foliage; its prolific production of shoots which make it capable of rapid reproduction; its consistency of large flower size even in warm weather; its pure white, evenly formed flowers with intense cinnamon fragrance and remarkable lasting qualities; its long bud which opens slowly and in a distinctive pinwheel formation; and the very heavy substance of its flower petals.

JOHN W. STEIDLE, Jr.